United States Patent [19]

Duffett

[11] Patent Number: Plant 6,050

[45] Date of Patent: Dec. 1, 1987

[54] CHRYSANTHEMUM PLANT NAMED KARDO

[75] Inventor: William E. Duffett, Salinas, Calif.

[73] Assignee: Yoder Brothers, Inc., Barberton, Ohio

[21] Appl. No.: 786,001

[22] Filed: Oct. 10, 1985

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Evans

[57] ABSTRACT

A Chrysanthemum plant named Kardo particularly characterized as to uniqueness by the combined characteristics of flat capitulum form; daisy capitulum type; yellow-orange ray floret color; diameter across face of capitulum of up to 11 cm at maturity; uniform nine week photoperiodic flowering response to short days; tall plant height when grown single stem; 18 to 33 cm peduncles on open, normally terminal sprays; slow development of green discs and 13° C. minimum temperature tolerance for initiation and development of flowering buds with a 12 to 13 hour continuous dark period.

3 Drawing Figures

The present invention comprises a new and distinct cultivar of Chrysanthemum, botanically known as *Dentrenthema morifolium*, Ramat., previously *Chrysanthemum morifolium*, Ramat., and referred to by the cultivar name Kardo.

Kardo, identified as 79L40001, was originated from a cross made in a controlled breeding program in Salinas, Calif., in 1979. The female parent of Kardo, identified as 75211A01, was the cultivar identified as White Nova, disclosed in U.S. Plant Pat. No. 5,289. The male parent of Kardo, identified as 78419004, was an unnamed seedling.

Kardo was discovered and selected as one flowering plant within the progeny of the stated cross by William E. Duffett in July of 1980, in a controlled environment in Salinas, Calif.

The first act of asexual reproduction of Kardo was accomplished when vegetative cuttings were taken from the initial selection in October of 1980 in a controlled environment in Salinas, Calif. by a technician working under formulations established and supervised by William E. Duffett.

Horticultural examination of controlled flowerings of successive plantings has shown that the unique combination of characteristics as herein disclosed for Kardo are firmly fixed and are retained through successive generations of asexual reproduction.

Kardo has not been observed under all possible environmental conditions. The phenotype may vary significantly with variations in environment such as temperature, light intensity and day length.

The following observations, measurements and comparisons describe plants grown in Salinas, Calif. and Bogota, Colombia under greenhouse conditions which approximate those generally used in commercial greenhouse practice.

The following traits have been repeatedly observed and are determined to be basic characteristics of Kardo which, in combination, distinguish this Chrysanthemum as a new and distinct cultivar:

(1) Flat capitulum form.
(2) Daisy capitulum type.
(3) Yellow-orange ray floret color.

(4) Diameter across face of capitulum up to 11 cm. at maturity.
(5) Uniform nine week photoperiodic flowering response to short days.
(6) Peduncle length ranging from 18 to 33 cm.
(7) Tall plant height, requiring one long day week prior to short days to attain a flowered plant height of 95 to 105 cm for year around flowering.
(8) Low temperature tolerance of 13° C. for initiation and development of flowering buds when grown in single stem cut spray programs with a continuous dark period of 12 to 13 hours.

The accompanying photographic drawings show typical inflorescence and leaf characteristics of Kardo, with the colors being as nearly true as possible with illustrations of this type.

Sheet 1 is a color photograph of Kardo grown as a single stem cut spray.

Sheet 2 is a black and white photograph of three views of the inflorescence of Kardo.

Sheet 3 is a black and white photograph showing the upper and under sides of the leaves of Kardo at three stages of development (mature, intermediate and immature).

Of the commercial cultivars known to the inventor, the most similar in comparison to Kardo is Amber, disclosed in U.S. Plant Pat. No. 3,969. Reference is made to attached Chart A, which compares certain characteristics of Kardo to the same characteristics of Amber. Similar traits are type, form, response and low temperature tolerance. Kardo develops a lighter ray floret color, longer peduncles, larger capitulum diameter and taller plant height than Amber.

In the following description, color references are made to The Royal Horticultural Society Colour Chart. The exact colors for corolla of ray florets are not precisely represented in The Royal Horticultural Society Colour Chart (RHS), and the colors given are the closest to the actual color of Kardo. The color values were determined on plant material grown in Salinas, Calif. on July 18, 1985.

Classification:

*Botanical.*—*Dentrenthema morifolium,* Ramat., cv Kardo.

*Commercial.*—Daisy cut spray mum.

I. INFLORESCENCE

A. Capitulum:

*Form.*—Flat.

*Type.*—Daisy.

*Diameter across face.*—Up to 11 cm at maturity.

B. Corolla of ray florets:

*Color (general tonality from a distance of three meters).*—Yellow-orange.

*Color (upper surface).*—Base color 19A to 20B, overlaid with 167B.

*Color (under surface).*—14C.

*Shape.*—Oblong.

C. Corolla of disc florets:

*Color (mature).*—14C.

*Color (immature).*—7A.

D. Reproductive organs:

*Androecium.*—Present disc florets only; moderate pollen.

*Gynoecium.*—Present both ray and disc florets.

II. PLANT

A. General appearance:

*Height.*—Tall; 95 to 105 cm. as a flowering plant from a rooted cutting with seven long days for year around flowerings maintaining a continuous dark period of 12 to 13 hours.

B. Foliage:

*Color (upper surface).*—147A.

*Color (under surface).*—137B–137C.

*Shape.*—Narrow, deeply lobed and sharply serrated.

CHART A

COMPARISON OF KARDO AND AMBER

| CULTIVAR | FLORET COLOR | CAPITULUM FORM AND TYPE | SPRAY FORMATION | DIAMETER ACROSS FACE OF CAPITULUM |
|---|---|---|---|---|
| KARDO | YELLOW-ORANGE | FLAT DAISY | 18 to 33 cm. PEDUNCLES | UP TO 11 cm. |
| AMBER | ORANGE | FLAT DAISY | 15 to 20 cm. PEDUNCLES | UP TO 8 cm. |

| CULTIVAR | PLANT HEIGHT | FLOWERING RESPONSE | LOW TEMPERATURE TOLERANCE |
|---|---|---|---|
| KARDO | TALL, 95 to 105 cm. | 9 WEEKS | 13° C. |
| AMBER | MEDIUM, 80 to 90 cm. | 9 WEEKS | 13° C. |

COMPARISONS MADE OF PLANTS GROWN AS SINGLE STEM CUT SPRAY MUMS WITH SEVEN LONG DAYS UB SALINAS, CALIFORNIA

I claim:

1. A new and distinct Chrysanthemum plant named Kardo, as described and illustrated, and particularly characterized as to uniqueness by the combined characteristics of flat capitulum form; daisy capitulum type; yellow-orange ray floret color; diameter across face of capitulum of up to 11 cm at maturity; uniform nine week photoperiodic flowering response to short days; tall plant height when grown single stem; 18 to 33 cm peduncles on open, normally terminal sprays; slow development of green discs; and 13° C. minimum temperature tolerance for initiation and development of flowering buds with a 12 to 13 hour continuous dark period.

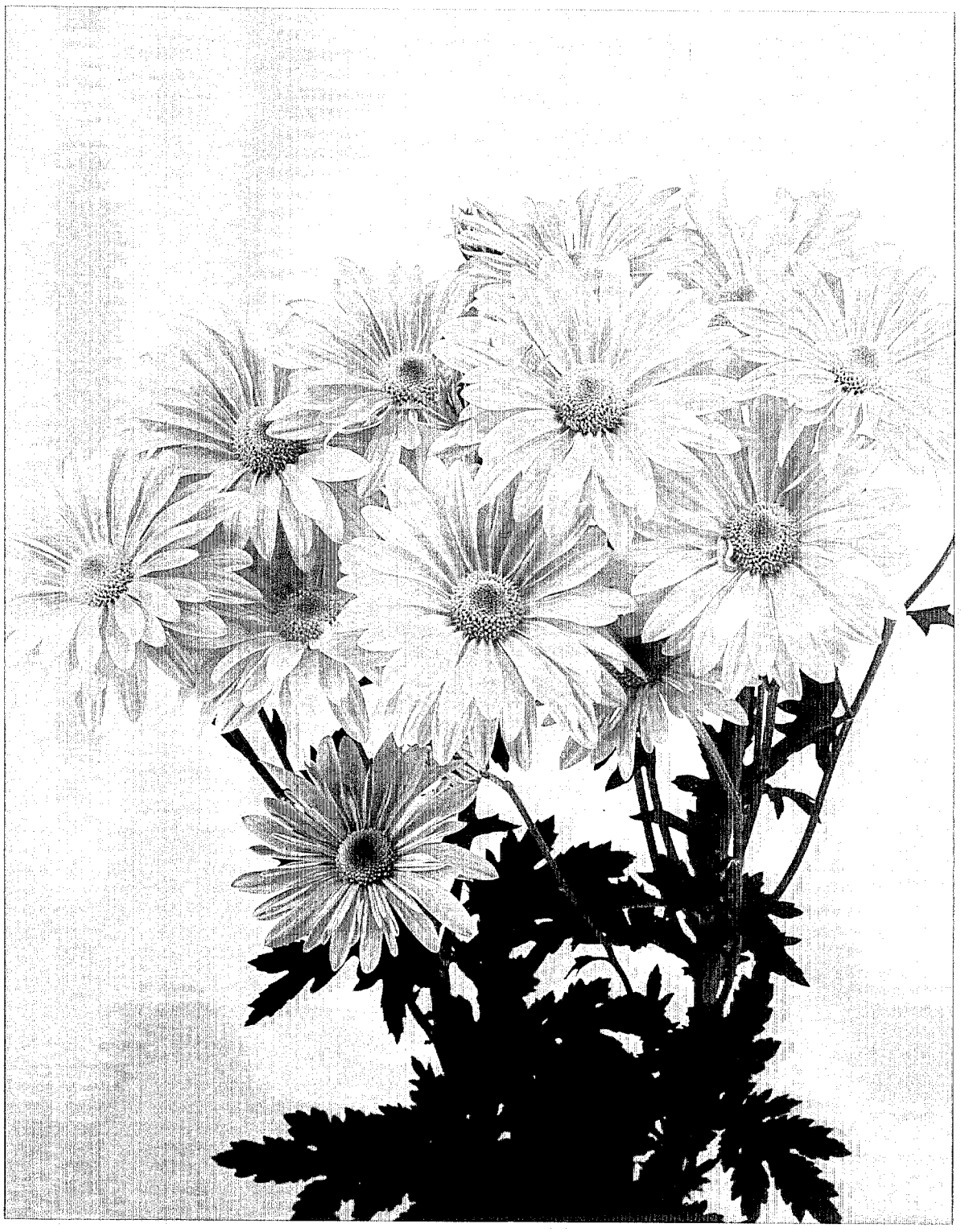

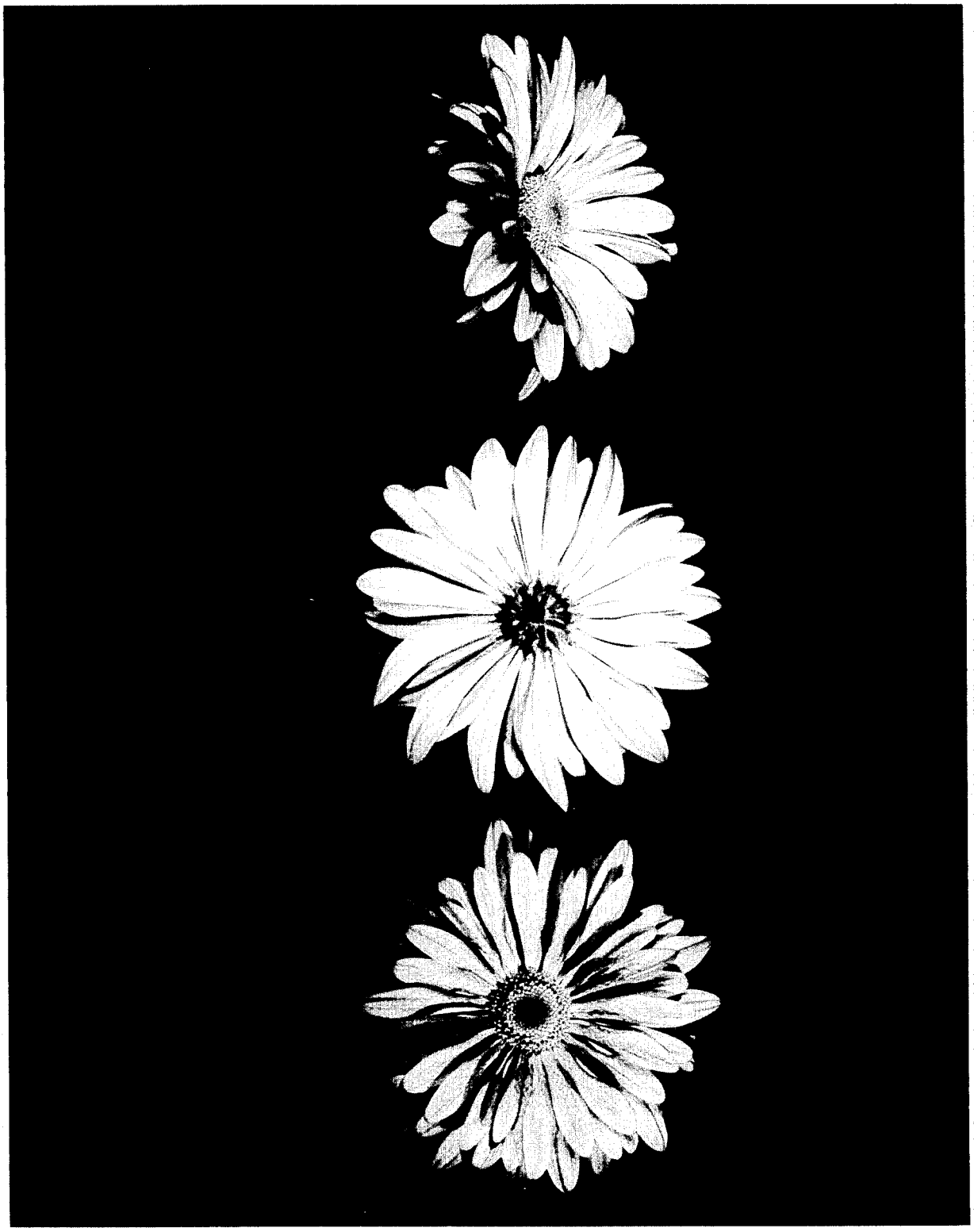

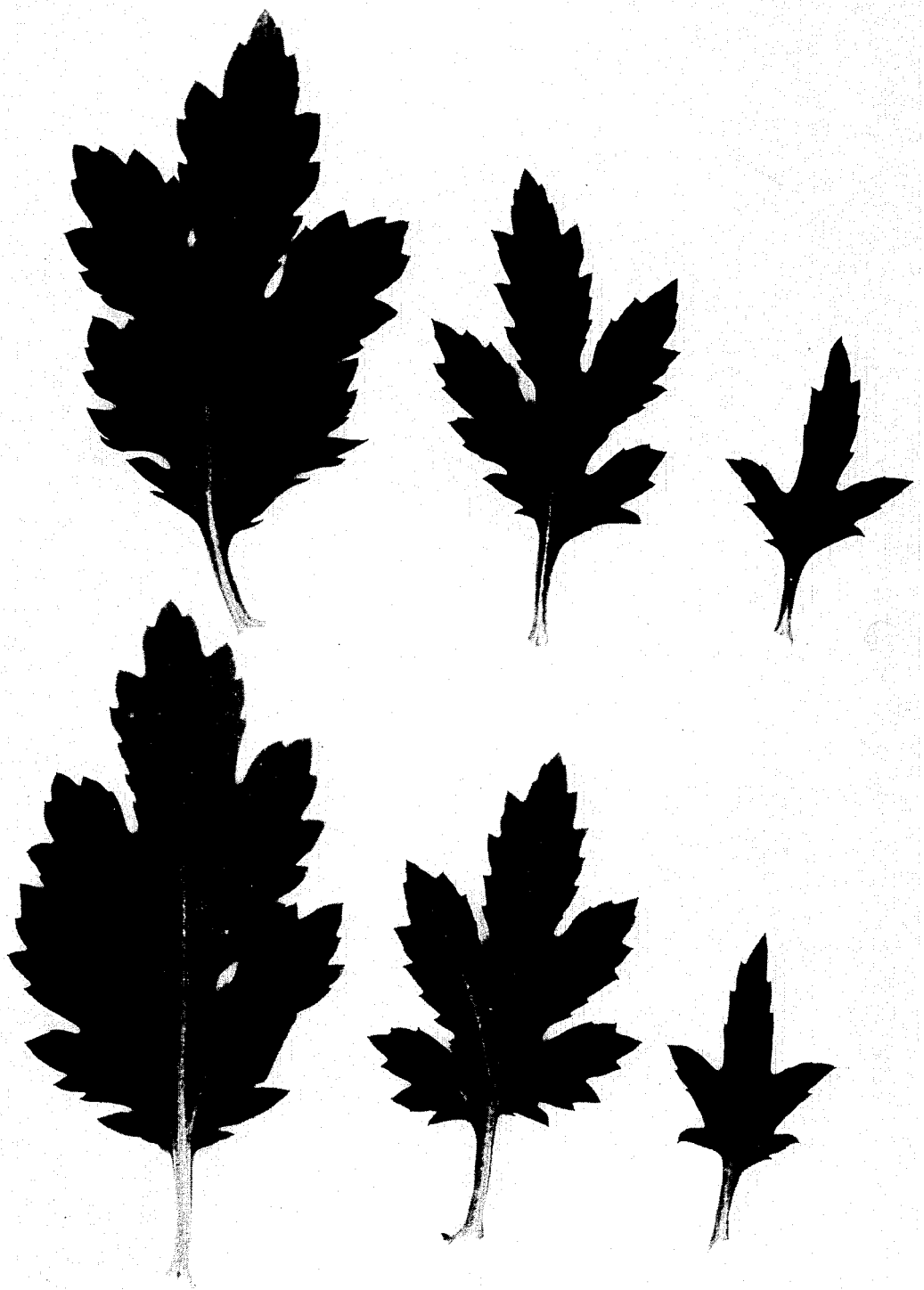

* * * * *